United States Patent [19]
Crass et al.

[11] Patent Number: 5,419,770
[45] Date of Patent: * May 30, 1995

[54] SELF PRIMING TUBING SET FOR AN INFUSION DEVICE

[75] Inventors: Richard E. Crass, San Diego; John S. Thompson, San Clemente, both of Calif.

[73] Assignee: Imed Corporation, San Diego, Calif.

[*] Notice: The portion of the term of this patent subsequent to Mar. 1, 2011 has been disclaimed.

[21] Appl. No.: 180,217

[22] Filed: Jan. 12, 1994

Related U.S. Application Data

[63] Continuation of Ser. No. 896,235, Jun. 10, 1992, Pat. No. 5,290,238.

[51] Int. Cl.⁶ ............................................. A61M 1/00
[52] U.S. Cl. .................................... 604/123; 604/126; 604/118
[58] Field of Search ............... 604/118, 122–126, 604/131–133, 135, 190, 246, 252, 257, 280; 128/DIG. 12

[56] References Cited

U.S. PATENT DOCUMENTS

| 3,590,640 | 7/1971 | Cindrich . |
| 3,803,810 | 4/1974 | Rosenberg ............................ 604/126 |
| 4,105,029 | 8/1978 | Virag ..................................... 604/122 |
| 4,146,028 | 3/1979 | LeFevre . |
| 4,244,365 | 1/1981 | McGill et al. . |
| 4,294,594 | 10/1981 | Sloane, Jr. et al. ................. 604/126 |
| 4,324,350 | 4/1982 | Thompson . |
| 4,391,599 | 7/1983 | Jenkins . |
| 4,419,096 | 12/1983 | Leeper et al. . |
| 4,446,991 | 5/1984 | Thompson . |
| 4,458,830 | 7/1984 | Werding . |
| 4,521,683 | 6/1985 | Miller . |
| 4,526,574 | 7/1985 | Pekkarinen . |
| 4,636,313 | 1/1987 | Vaillancourt . |
| 4,702,397 | 10/1987 | Gortz . |
| 4,813,937 | 3/1989 | Vaillancourt . |
| 4,863,429 | 9/1989 | Baldwin . |
| 4,904,239 | 2/1990 | Winchell et al. . |
| 4,909,790 | 3/1990 | Tsujikawa et al. . |
| 5,080,652 | 1/1992 | Sancoff et al. ...................... 604/132 |
| 5,106,374 | 4/1992 | Apperson et al. ........... 128/DIG. 12 |
| 5,167,631 | 12/1992 | Thompson . |

FOREIGN PATENT DOCUMENTS

0302722A2  2/1989  European Pat. Off. .
WO86/02978 7/1986  WIPO .

Primary Examiner—C. Fred Rosenbaum
Assistant Examiner—Frank Wilkens, III
Attorney, Agent, or Firm—Nydegger & Associates

[57] ABSTRACT

A self priming tubing set for infusing a medical solution from an infusion device to a patient includes a supply tube, an air/particle filter, and a restrictor tube. The air/particle filter is adapted to remove air, particularly air contained in the supply tube at the initiation of fluid flow. The air/particle filter also removes particles from the medical solution. The restrictor tube is adapted to reduce the pressure of the medical solution from the delivery pressure of the infusion device to about a mean venous pressure of the patient. The length and inside diameter of the restrictor tube are calibrated to achieve a desired pressure drop dependent on design criteria of the system. The tubing set also includes a slide clamp for closing fluid flow from the supply tube and a connector for connection to a patient interface such as a hypodermic needle or cannula.

5 Claims, 2 Drawing Sheets

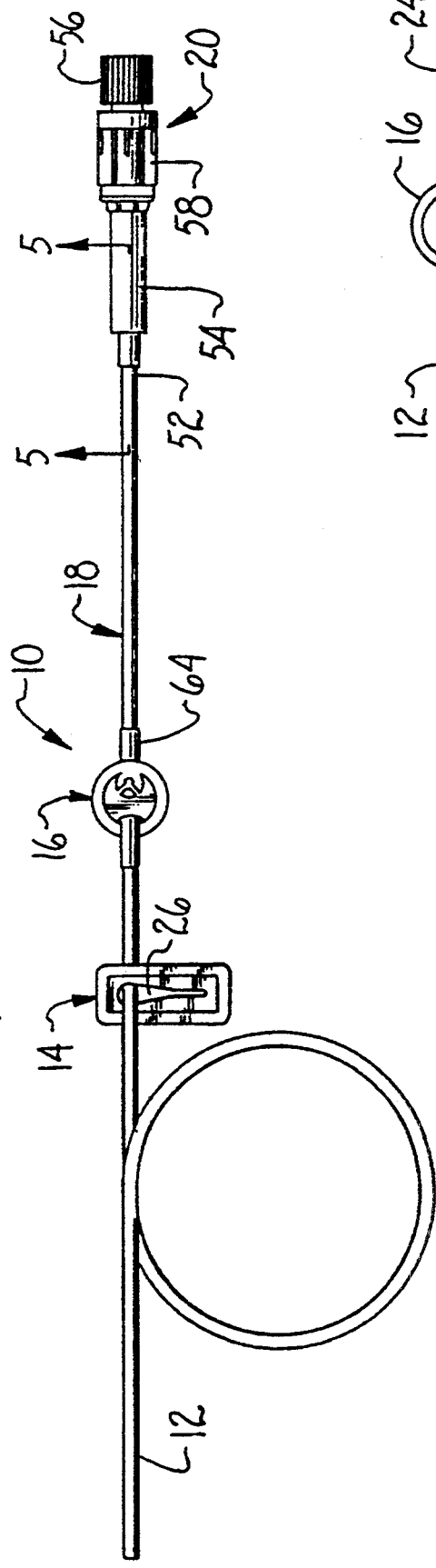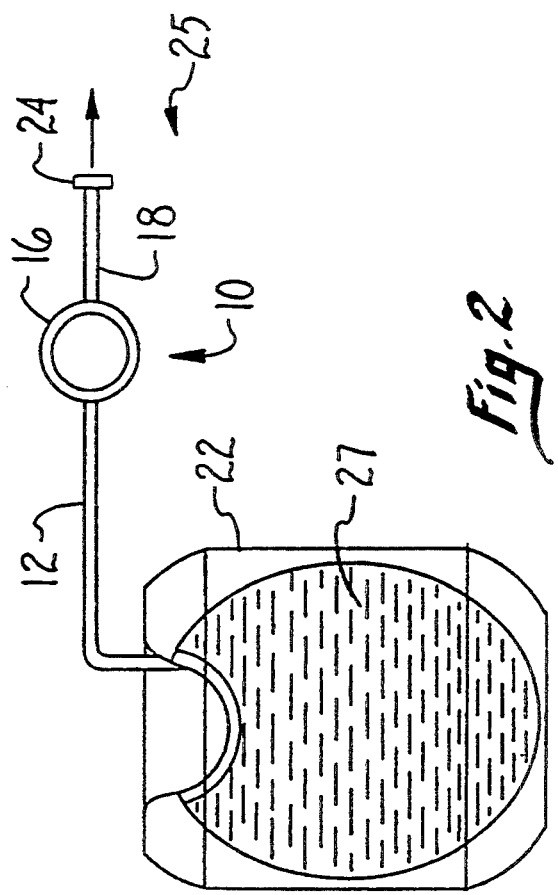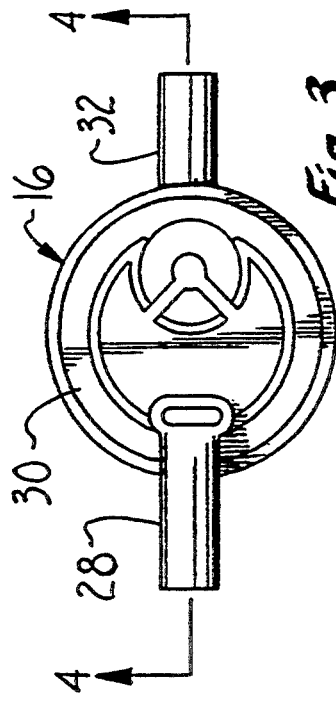

SELF PRIMING TUBING SET FOR AN INFUSION DEVICE

This is a continuation of co-pending application Ser. No. 07/896,235, entitled "Self Priming Tubing Set for an Infusion Device", filed Jun. 10, 1992, (now U.S. Pat. No. 5,290,238).

TECHNICAL FIELD

The present invention relates to medical devices. More particularly the present invention pertains to infusion devices for intravenously infusing medical solutions into a patient. The present invention is particularly, but not exclusively, useful as a tubing set for an elastomeric infusion device.

BACKGROUND OF THE INVENTION

With recent advances in medical technology, increased emphasis has been placed on medical equipment and techniques that can be used and performed by patients on an outpatient or home care basis. As an example, some infusion therapy programs can now be administered at home by a patient or by medical personnel having a minimum of training.

Some infusion therapy is accomplished using an IV administration set. Such an administration set typically includes a patient interface device such as a hypodermic needle which is inserted at a venous access site on the patient. The hypodermic needle is connected to a flexible supply tube which in turn, is connected to a supply of the medical solution. The medical solution may be dispensed by gravity from a bag suspended from a pole or by an infusion device such as a peristaltic or volumetric pump coupled to a supply of the medical solution.

Recently, elastomeric infusion devices have been utilized for dispensing medical solutions. Such elastomeric infusion devices are simpler in construction and more adaptable to home use than peristaltic pumps. An elastomeric infusion device typically includes a supply of the medical solution which is pressurized by an elastomeric membrane. In use, the medical solution is forced by the elastomeric membrane through the supply tube and into the patient. Preferably, the delivery pressure is relatively constant over the range of delivery. Such devices may be portable and disposable and in general are adaptable to use on either an inpatient or outpatient states.

As an example, a disposable elastomeric infusion system is marketed by IMED corporation, San Diego, Calif. assignee of the present application under the trademark ReadyMed 100/200.

The use of such elastomeric infusion devices, as well as use of other types of IV administration sets, requires that the supply tube be purged of air or "primed" prior to initiation of fluid flow through the supply tube and into the patient. This is because the supply tube prior to activation of the infusion device contains a dead space volume of air. A priming procedure for purging the supply tube of this volume of air must typically be performed prior to connection of the supply tube to the patient interface device (i.e. hypodermic needle) of the IV administration set.

Initially, the proximal end of the supply tube is attached to the supply reservoir of the elastomeric infusion device. The distal end of the supply tube is initially closed off using a tube clamp. For priming the supply tube, the tube clamp is adjusted, opening the supply tube and initiating fluid flow from the supply reservoir of the elastomeric infusion device and through the supply tube. This forces the dead volume of air initially contained in the supply tube out the distal end of the supply tube. When fluid reaches the distal end of the supply tube, the air in the supply tube has been purged. The supply tube is then closed off by adjusting the tube clamp and the distal end of the supply tube is attached to the patient interface device.

This procedure may be difficult to perform and time consuming for a patient or relatively unskilled medical personnel. Moreover, if the priming procedure is not performed correctly it may cause the elastomeric infusion device to function improperly. In addition, incorrect application of the procedure may have serious medical consequences for the patient, such as the introduction of excessive air and other contaminants into the vein.

Another consideration with the use of such an elastomeric infusion device is in the need to provide a constant or predictable fluid delivery pressure regardless of the quantity of solution remaining in the infusion device. In addition, the delivery pressure of the solution exiting the infusion device may be substantially higher than a desired pressure at the patient interface (i.e. hypodermic needle) and accordingly must be reduced. As an example, it is desirable to deliver most medical solutions to the patient at a pressure that is slightly greater than the mean venous pressure of the patient.

In light of the above, there is a need in the art for a tubing set that can be used with an elastomeric infusion device to provide a constant fluid delivery pressure without the need for priming the supply tube from the infusion device. Accordingly it is an object of the present invention to provide a tubing set for an infusion device for infusing medical solutions that provides a relatively constant pressure drop at constant flow and that is self priming. It is a further object of the present invention to provide a tubing set having a filter element that removes air and particles from the medical solution to be infused. It is another object of the present invention to provide a tubing set for use with an infusion device in which a minimal dead space volume is provided between the filter element of the tubing set and a patient interface device such as a hypodermic needle at a venous access site of a patient. It is yet another object of the present invention to provide a tubing set that can be calibrated for reducing the pressure from an elastomeric infusion device to just above the venous pressure of the patient. It is a further object of the present invention to provide a tubing set that is easy to use, simple in construction, and relatively inexpensive to manufacture.

SUMMARY OF THE INVENTION

In accordance with the present invention a self priming tubing set for use with an infusion device for medical solutions, and particularly elastomeric infusion devices, is provided. The tubing set is adapted to connect at an upstream end to the infusion device and at a downstream end to a patient interface device such as a hypodermic needle, a PICC line or a patient access cannula. The tubing set includes, a supply tube for connection to the infusion device, an air/particle filter connected to the supply tube for removing air and solid particles from the medical solution, and a length of restrictor tube for reducing the delivery pressure of the medical solution to the patient. The tubing set also includes a slide clamp operatively associated with the supply tube to selectively occlude the supply tube and prevent fluid flow from the infusion device to the patient. In addition a connector is attached to the distal end of the restrictor tube for connecting the tubing set to the patient interface device.

The tubing set also includes a slide clamp that functions to selectively close the supply tube and prevent fluid flow from the infusion device to the patient. Also included, is a connector at distal end for connecting to the patient interface device.

The supply tube is formed of a large bore medical tubing that connects to the infusion device and to the air/particle filter. The air/particle filter is constructed with an air filter element having a bubble point that exceeds the upstream pressure of the elastomeric infusion device under all conditions of use. As such the air/particle filter is constructed with an air filter formed of a hydrophobic material such as Goretex ™ which allows the passage of air and vapor through a vent but restricts the passage of the liquid medical solution. The air/particle filter is also constructed with a particle filter formed of a hydrophilic material such as a Sartorius ™ membrane adapted to remove particles from the medical solution having a size of more than about one micron.

The restrictor tube is a length of tubing located between the air/particle filter and the distal end of the tubing set. The restrictor tube is constructed as a relatively short length of tubing and has a relatively small diameter to minimize the dead space volume below or downstream from the air/particle filter. In an illustrative embodiment this dead space volume is less than dead space volume of similar prior art devices and is on the order of about 75 microliters. The restrictor tube also functions to reduce the fluid pressure from the infusion device to provide a lower pressure at the venous access site.

In use, the tubing set can be connected to an elastomeric infusion device such as a medical solution supply reservoir which includes an elastomeric bladder to pressurize the fluid. The air/particle filter of the tubing set removes any air present in the supply line between the elastomeric infusion device and the air filter. This is the self priming function of the tubing set. In addition the tubing set is adapted to reduce the pressure created by the elastomeric infusion device during infusion. Specifically, a length and diameter of the tubing set is calibrated to reduce the fluid pressure from the internal mean pressure of the elastomeric infusion device to about the mean venous pressure of the patient.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts.

FIG. 1 is a side elevation view of a tubing set constructed in accordance with the present invention;

FIG. 2 is a schematic diagram of a total infusion system that includes an elastomeric infusion device and a tubing set constructed in accordance with the present invention;

FIG. 3 is a plan view of an air/particle filter element of the tubing set shown in FIG. 1;

DESCRIPTION OF PREFERRED EMBODIMENTS

Figure 6:
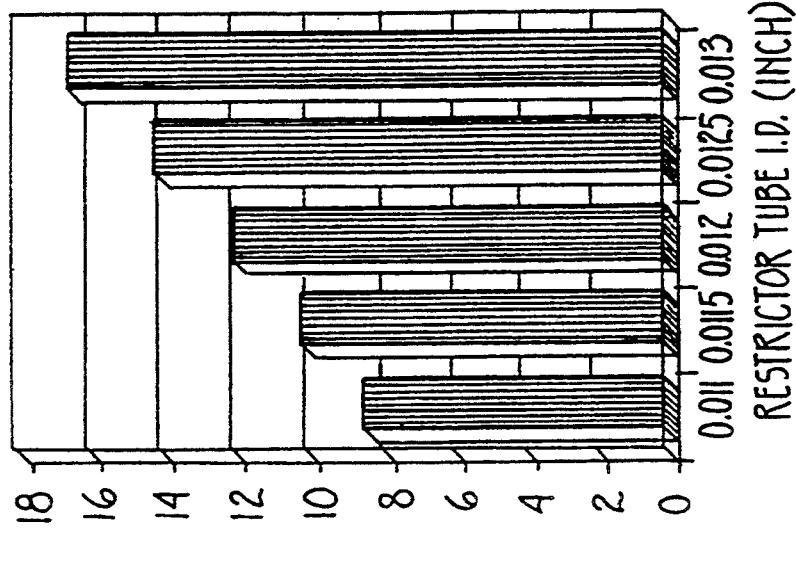
FIG. 6 is a graph for determining the length and diameter of the restrictor tube for a particular infusion device.

Referring now to FIG. 1 a tubing set constructed in accordance with the invention is shown and generally designated as 10.

The tubing set 10, generally stated, includes a supply tube 12, a slide clamp 14, an air/particle filter 16, a length of restrictor tube 18 and a connector 20. The supply tube 12 connects to an elastomeric infusion device 22 to provide a fluid conduit from the infusion device 22. The slide clamp 14 is mounted to the supply tube 12 to selectively occlude and prevent fluid flow through the supply tube 12. The air/particle filter 16 removes air present in the supply tube 12 and any particles present in the medical solution. The restrictor tube 18 functions to reduce the delivery pressure of the medical solution to about the mean venous pressure of the patient regardless of the quantity of fluid present in the infusion device 22. The connector member 20 connects the tubing set 10 to a patient interface device 24 such as to a hypodermic needle or supply cannula (not shown).

With reference to FIG. 2, an infusion system 25 includes the elastomeric infusion device 22, having a quantity of a medical solution 27 to be infused into a patient (not shown). Such a medical solution may as an example be saline, antibiotics, heparin or other medical solution depending on the treatment. The infusion system 25 also includes the tubing set 10 (i.e. the supply tube 12, the air/particle filter 16, the restrictor tube 18, and the connector member 20) and a patient interface device 24. The patient interface device 24 may be a hypodermic needle, cannula or PICC line coupled to the connector 20 of the tubing set 10 and to a venous access device of the patient.

The elastomeric device 22 is constructed to supply an exact quantity of a medical solution to a patient. As an example, such an elastomeric device may be similar to one distributed by IMED Corporation, San Diego, Calif., assignee of the present application, and sold under the trade name ReadyMed. Alternately the supply of medical solution may be from other types of elastomeric devices or mechanical pumps which supply the medical solution.

The supply tube 12 is a length of medical tubing adapted for use as a conduit for medical fluids (i.e. saline, antibiotics, etc.). The main function of the supply tube 12 is to provide a conduit for fluid flow from the infusion device 22 to the patient. In addition, the inside diameter of the supply tube 12 can be selected to provide a pressure drop that is compatible with the design criteria of the total infusion system 25 of which the tubing set 10 is a part. By way of example and not limitation, the tube ID may be a relatively large bore in the range of 0.037 inches to 0.043 inches.

The length of the supply tube 12 will also depend on a desired overall length between the elastomeric infusion device 22 and the patient interface device 24. Typically this overall length will be on the order of about 48 inches. By way of example and not limitation, to achieve this overall length the length of the supply tube 12 will be on the order of about 32 to 39 inches.

The supply tube 12 will have a relatively larger inside diameter than the length of restrictor tubing 18. Most of the pressure drop between the infusion device 22 and the patient interface 24 will be achieved and controlled by the restrictor tubing 18.

With reference to FIG. 1, the slide clamp 14 is adapted to fit on the supply tube 12 for occluding the supply tube 12 and preventing fluid flow from the infusion device 22. Such slide clamps 14 are well known in the art. The slide clamp 14 is formed with an elongated tapered opening 26 having a large portion and a narrow portion, substantially as shown in FIG. 1. In use of the slide clamp 14, for closing the supply tube 12, the narrow portion of the tapered opening 26 is slid over the supply tube 12. This restricts or occludes the supply tube 12. For opening the supply tube 12 the slide clamp 14 is positioned with the large portion of the tapered opening 26 over the supply tube 12.

Figure 4:
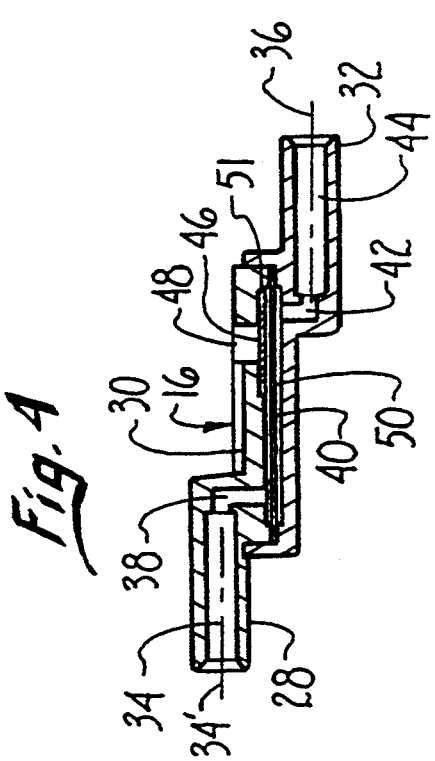
FIG. 4 is a cross sectional elevation view taken along section line 5—5 of FIG. 4.

Referring now to FIGS. 3 and 4 the construction of the air/particle filter 16 is shown. The air/particle filter 16 includes a hydrophobic air filter element 46 adapted to remove any air in the tubing set 10 upstream from the location of the air filter 16. This is most likely air that is entrained within the supply tube 12 prior to initiation of fluid flow from the infusion device 22 through the tubing set 10. The air/particle filter also includes a hydrophilic particle filter element 50 adapted to remove any particles contained in the medical solution. The air/particle filter 16 also includes an inlet section 28, a main body portion 30, and an outlet section 32. It is important to note that the internal pressure of the elastomeric infusion device 22 must be below the bubble point of the air particle filter 16 or air will pass through the hydrophilic particle filter element 50 and to the patient.

The inlet section 28 of the air/particle filter 16 is adapted to be permanently connected to the supply tube 12 of the tubing set 10. This connection may be accomplished using an adhesive such as cyclohexanone. The inlet section 28 includes a fluid passageway 34 that extends along a longitudinal axis 34' of the inlet section 28. Fluid passageway 34 may be chamfered as shown in FIG. 4 for receiving the supply tube 12 (FIG. 1).

The fluid passageway 34 of the inlet section 28 intersects with a second fluid passageway 38 that extends generally perpendicular to the longitudinal axis 34' of the inlet section 28. The second fluid passageway 38 in turn connects to a central fluid passageway 40 through the main body portion 30 of the air/particle filter 16.

The inlet section 28 may be formed as a unitary section with an outer peripheral configuration substantially as shown in FIG. 3 for a mating connection with the main body portion 30 of the air/particle filter 16. The main body portion 30 of the air/particle filter 16 is also of a one piece mating construction and is formed integrally with the outlet section 32. The inlet section 28 and main body portion 30 may be injection molded of a material such as an acrylic that is suitable for contact with medical solutions. The inlet section 28 is joined to the main body portion 30 of the air/particle filter 16 after assembly of the filter elements to be hereinafter described. An adhesive or ultrasonic weld may be used to attach the inlet section 28 to the main body portion 30 to complete the assembly of the air/particle filter 16.

The main body portion 30 of the air/particle filter 16 includes the central passageway 40 and a secondary fluid passageway 42 that connects to the central passageway 40 in a direction generally perpendicular to a longitudinal axis of the central passageway 40. The secondary fluid passageway 42 in turn connects to a fluid passageway 44 through the outlet section 32. Fluid passageway 44 is generally perpendicular to fluid passageway 42.

Fluid entering the air/particle filter 16 follows a tortuous path through the air/particle filter 16. Starting with entry into fluid passageway 34 of the inlet section 28, the direction of fluid flow is turned 90 degrees into fluid passageway 38. From fluid passageway 38 fluid flow is again turned 90 degrees into central passageway 40 of the main body portion 30. From central fluid passageway 40, fluid flow is then turned 90 degrees into fluid passageway 42. Finally, fluid flow is turned 90 degrees again into fluid passageway 44 and exits from the outlet section 32 in the same direction it originally entered the inlet section 28 of the air/particle filter 16.

Figure 5:
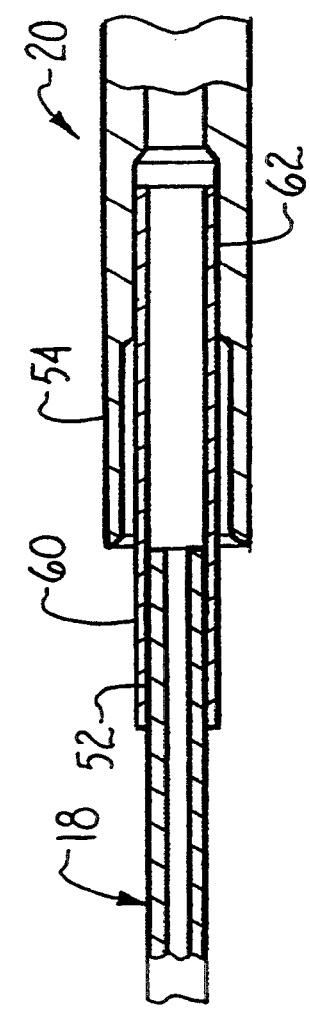
FIG. 5 is a cross sectional elevation view taken along section line 4—4 of FIG. 3.

The outlet section 32 of the air/particle filter 16 is adapted to be permanently connected to the restrictor tubing 18 of the tubing set 10 in flow communication therewith. An adhesive such as cyclohexanone may be utilized to connect the restrictor tubing 18 to the outlet section. As shown in FIG. 5, the outlet section 32 is formed integrally with the main body portion 30 of the air/particle filter 16. In addition, the end of the fluid passageway 44 through the outlet section may be chamfered for receiving the restrictor tubing 18.

The main body portion 30 of the air/particle filter 16 in addition to the structure previously described, includes, the hydrophobic air filter element 46, an air passageway 48 and the hydrophilic particle filter element 50 mounted therein. The hydrophobic air filter element 46 and air passageway 48 function to purge any air in the system upstream from the air filter 16 (i.e. air entrained in the supply tube 12 at start up). The hydrophilic particle filter element 50 functions to remove any solid particles contained in the medical solution to be infused.

The hydrophilic particle filter element 50 extends the length of the central passageway 40 substantially as shown in FIG. 4. Any fluid flowing from passageway 34 of the inlet section 28 through passageway 42 to the outlet section 32 must pass through the hydrophilic particle filter element 40. The particle filter element 50 may be formed of a hydrophilic filter media adapted to remove particles having a size on the order of a micron. One suitable particle filter media is Sartorius TM material having a rating of 1.2 microns. Such a filter media may be mounted on a suitable frame. This type of filter may be purchased from Filtertek, Inc., Hebron, Ill. The particle filter is clamped between the inlet section 28 and main body portion 30 of the air/particle filter 16 during assembly of the air/particle filter 16.

The hydrophobic air filter element 46 is mounted within a counterbore 51 formed in the main body 30 substantially flush with the sidewall of the central passageway 40. The air filter element 46 is thus in flow contact with fluids flow through the central passageway 40 on one side and in contact with the air passageway 48 on the opposite side.

The hydrophobic air filter element 46 is a thin patch of filter material generally circular in shape. The hydrophobic air filter element 46 may be attached to the counterbore 51 and to the main body 30 of the air/particle filter 16 using an adhesive or clamping arrangement or an ultrasonic weld. The air vent 48 extends through the sidewall of the main body 30 along an axis generally coincident with the center of the counterbore 51 and circular air filter element 46.

The air filter element 46 may be formed of a material having a structure that allows gaseous and vapor molecules to pass through the material but which is impervious to liquid molecules. A high tech woven fabric material having very small openings can be used as such a filter element. As an example the openings may be on the order of about 0.02 microns in size. One such suitable material is Goretex TM manufactured by The Gore Company. Such an integrated filter may be purchased from Filtertek, Inc., Hebron, Ill.

With this arrangement air molecules can be pushed by the flow of the liquid medical solution in the central passageway 40 of the air/particle filter 16, through the hydrophobic air filter element 46 and through the air passageway 48 to the atmosphere. The liquid medical solution, on the other hand, can not penetrate the air filter element 46 and will continue to flow within the central fluid passageway 40 of the air/particle filter 16. Because the bubble point of the air/particle filter 16 exceeds the upstream pressure of the elastomeric infusion device 22 under all conditions of use, substantially all air will be vented from the medical solution.

The construction and location of the air filter element 46, with respect to passageway 38 and central passageway 40, is such that a portion of the air filter element 46 is situated normal to the direction of fluid flow from passageway 38 of the inlet section 28 of the air/particle filter 16. This helps to direct all of the air flowing through the air/particle filter 16 through the air filter element 46. In addition, the changing direction of flow helps expose any air entrained in the flow of liquid through the air/particle filter 16 to contact the air filter element 46. Moreover, a portion of the air filter element 46 channels fluid flow along the central passageway 40 to provide even more contact between the filter element 46 and any air moving through the central passageway 40.

Referring now to FIG. 5 and also back to FIG. 1 the construction of the restrictor tube 18 will be explained. As previously stated, the restrictor tube 18 functions to drop the pressure of the medical solution from the delivery pressure of the elastomeric infusion device 22 (FIG. 2) to about and slightly above the mean venous pressure of the patient. The length and inside diameter of the restrictor tube 18 are calibrated such that a desired pressure drop is achieved substantially independent of the initial delivery pressure. A predetermined delivery pressure is thus provided at the patient interface device 24 (FIG. 2).

In addition to this function, the restrictor tube 18 functions to provide a connecting section between the air/particle filter 16 and the patient interface device 24 (FIG. 2) that has a minimal volumetric capacity. This helps to reduce the dead volume of air downstream from the air/particle filter 16 at start up. This dead volume of air must be below the limit of "bubble size" for the elastomeric infusion device 22 (FIG. 2). For commercially available elastomeric infusion devices, such as those previously described, the limit of bubble size is on the order of about 75 microliters.

As shown in FIG. 1, the restrictor tube 18 is connected at its proximal or upstream end 64 to the outlet section 32 of the air/particle filter 16. The distal end or downstream 52 of the restrictor tube 18 is connected to the connector 20 that connects to the patient interface 24. As an example the connector 20 shown in FIG. 1 may be a male non rotating luer 54 having a protective cap 56 and a nut 58.

FIG. 5 illustrates the connection of the restrictor tube 18 to the rotating luer 54 of the connector 20. As shown, the rotating luer 54 includes a sleeve 60 that connects to a bore 62 within the luer 54. The distal or downstream end 52 of the restrictor tube 18 fits within the inside diameter of the sleeve 60 to form a fluid tight connection. The outside diameter of the restrictor tube 18 thus closely matches the inside diameter of the sleeve 60 to provide a press fit.

The length and inside diameter of the restrictor tube 18 are selected to provide a desired pressure drop between the infusion device 22 (FIG. 2) and the patient interfaces device 24. In general this pressure drop is dependant not only on the delivery pressure of the elastomeric infusion device 22 but on the length and diameter of the supply tube 12, on the fluid viscosity of the medical solution and on the flow characteristics of the air/particle filter 16. The restrictor tube 18 may be constructed, however, to provide a desired delivery pressure that is relatively constant over a wide range of delivery pressure for the elastomeric infusion device 22. A design theory for a tubing set 10 constructed in accordance with the invention is as follows.

With reference to FIG. 2, in the region of laminar flow, the tubing set 10 obeys Pouiselle's law for horizontal tubes; flow is directly proportional to the pressure drop and the particular conduits diameter to the fourth power, and inversely proportional to the fluid, viscosity, and length of cylindrical conduit. Additionally, the air/particle filter 16 acts as a constant resistor which increases the pressure drop. An infusion system is modeled by the following relationship.

$\Delta P = Q * R_t$ where Q=Flow (ml/hr)

$\Delta P$=Mean pressure drop from the elastomeric infusion device 22 to the patient (PSIG)

$R_t$=Total fluid resistance of system (PSIG - hr/ml)

The resistance of the system is the sum of the series resistors which include the supply tube 12 resistance (R1), the air/particle filter 16 resistance (R2), the restrictor tube 18 resistance (R3), and the patient interface 24 resistance (R4) (i.e. needle or PICC line).

$$R = \frac{128 * \mu * L}{\pi * g_c * D^4}$$

$\mu$=Fluid Viscosity
L=Conduit Length
$g_c$=Gravitational Constant
D=Conduit Diameter
R=Conduit Resistance
The system is described as:

$$\Delta P = \left( \frac{128 * \mu}{\pi * g_c} \left[ \left( \frac{L_c}{D_L^4} + \frac{L_t}{D_T^4} + \frac{L_R}{D_R^4} \right) + R_F \right] \right)$$

where;
$L_c$=Length of patient cannula interface
$L_t$=Length of larger bore tubing
$L_R$=Length of restrictor tubing
$D_L$=diameter of patient cannulas
$D_T$=Diameter of larger bore tube
$D_R$=Diameter of restrictor tube
$R_F$=Filter resistance empirically determined as 0.000602 PSIG - hr/ml These formulae may be used to determine the pressure drops occurring throughout the system. In addition, these formulae can be used to formulate simple computer programs to calculate critical design variables such as the length of the supply tube 12 and the length and diameter of the restrictor tube 18. By way of example certain design criteria for the system may also be specified.

The following design criteria are by way of example and not limitation. An elastomeric infusion device 22 will have a mean fluid delivery pressure on the order of about 6 psig. The tubing set 10 design must reduce this delivery pressure to about the mean venous pressure of the patient which is estimated to be about 0.005 PSIG (i.e. 4 mmHg). The flow is to maintained at a constant rate of 100/mlhr at room temperature using diluent 0.9N saline with antibiotic. Coupled to the tubing set 10 is the patient interface device 24 which may be anywhere from an 18 gauge to a 22 gauge needle to a PICC 60 cm in length.

While the particular Self Priming Tubing Set for an Infusion Device as herein shown and disclosed in detail is fully capable of obtaining the objects and providing the advantages herein before stated, it is to be understood that it is are merely illustrative of the presently preferred embodiments of the invention and that no limitations are intended to the details of construction or design herein shown other than as described in the appended claims.

We claim:

1. A self priming tubing set for infusing a medical solution from an elastomeric infusion device into a patient at an infusion pressure, said tubing set comprising:
   - a supply tube, said supply tube having an inner diameter of about 0.038 inch to about 0.042 inch and a length of about 32 inches to about 38 inches, said supply tube having an upstream end and a downstream end, said upstream end connectable with said elastomeric infusion device;
   - an air/particle filter having an inlet section connected to said downstream end of said supply tube, an outlet section, and a main body section having an air filter element and a particle filter element mounted therein, with said air/particle filter adapted to provide a tortuous path for fluid flow, and with said air filter element situated to contact and remove air from the fluid flow and said particle filter element in contact with fluid flow to remove particles from said medical solution;
   - a restrictor tube having an upstream end connected to said outlet section of said air/particle filter, said restrictor tube receiving said medical solution at an input pressure, and said restrictor tube having an inside diameter of between about 0.011 inches to about 0.013 inches and a length of about 8 inches to 18 inches thereby lowering the input pressure of said medical solution to said infusion pressure which is above a mean venous pressure of said patient; and
   - a connector connected to said downstream end of said restrictor tube, said connector connectable to a patient interface device.

2. The tubing set as claimed in claim 1, wherein said restrictor tube has a volume less than about 75 microliters.

3. A self priming tubing set for use with an elastomeric infusion device for infusing medical solutions from the infusion device into a patient comprising:
   - a supply tube connectable for fluid communication with said elastomeric infusion device, said supply tube having an inside diameter of about 0.038 inch to about 0.042 inch and a length of about 32 inches to about 38 inches;
   - an air/particle filter in fluid communication with said supply tube for removing air from said supply tube and particles from said medical solution, said air/particle filter including an inlet section connected to said supply tube, an air filter element connected to an air vent in fluid contact with said medical solution, a particle filter element in fluid contact with said medical solution, and an outlet section;
   - a restrictor tube in fluid communication with said outlet section of said air/particle filter, said restrictor tube providing a constant pressure drop at a constant flow of said medical solution, wherein the length of said restrictor tube is between 8.43 inches and 16.44 inches, and wherein the inside diameter of said restrictor tube is between 0.011 inches and 0.013 inches; and
   - a connector connected to a distal end of said restrictor tube and adaptable for connection to a patient interface.

4. The tubing set as claimed in claim 3, wherein a total pressure drop from said elastomeric infusion device to said patient interface is about 6 PSIG.

5. The tubing set as claimed in claim 3, wherein said restrictor tube has a volume less than about 75 microliters.

* * * * *